(12) United States Patent
McKie et al.

(10) Patent No.: US 6,913,711 B2
(45) Date of Patent: Jul. 5, 2005

(54) CORROSION INHIBITORS

(75) Inventors: Derrick B. McKie, Brooklyn, NY (US); Freda Robinson, Nyack, NY (US); Philip Franco, Ocean Grove, NJ (US)

(73) Assignee: Avon Products, Inc., New York, NY (US)

(*) Notice: Subject to any disclaimer, the term of this patent is extended or adjusted under 35 U.S.C. 154(b) by 562 days.

(21) Appl. No.: 09/741,490

(22) Filed: Dec. 19, 2000

(65) Prior Publication Data

US 2002/0125462 A1 Sep. 12, 2002

(51) Int. Cl.$^7$ ................................ C23F 11/00
(52) U.S. Cl. ................ 252/389.2; 424/47; 424/59; 424/65; 424/70.4; 424/70.9; 424/70.23; 424/76.4; 424/126; 424/601; 512/1
(58) Field of Search ................ 424/47, 59, 65, 424/70.4, 70.9, 70.23, 76.4, 121, 601; 512/1; 252/389.2

(56) References Cited

U.S. PATENT DOCUMENTS

| | | |
|---|---|---|
| 3,992,318 A | 11/1976 | Gaupp et al. |
| 4,052,160 A | 10/1977 | Cook et al. |
| 4,240,925 A | 12/1980 | Tait |
| 4,440,721 A | 4/1984 | Wilson et al. |
| 4,548,787 A | 10/1985 | Wilson et al. |
| 6,368,575 B2 * | 4/2002 | Chang .................... 424/47 |

FOREIGN PATENT DOCUMENTS

| | | | |
|---|---|---|---|
| CS | 244376 | | 6/1988 |
| CS | 262475 | | 7/1989 |
| DE | 3905299 | * | 8/1999 |
| JP | 62129399 | * | 6/1987 |
| JP | 03020205 | * | 1/1991 |
| JP | 07258045 | * | 10/1995 |
| JP | 07316031 | * | 12/1995 |
| JP | 409052814 | * | 2/1997 |
| JP | 11061197 | * | 3/1999 |

* cited by examiner

*Primary Examiner*—Cephia D. Toomer
(74) *Attorney, Agent, or Firm*—Ohlandt, Greeley, Ruggiero & Perle LLP

(57) ABSTRACT

There is provided a cosmetic or topical composition for use on the human body having a phosphate compound in an amount effective to inhibit corrosion of metallic containers containing the composition. Preferably, such a cosmetic or topical composition has sodium hydrogen phosphates and/or sodium polyphosphates in an amount about 0.05 wt % to about 1.5 wt % based on the total weight of the finished composition.

29 Claims, No Drawings

CORROSION INHIBITORS

BACKGROUND OF THE INVENTION

1. Field of the Invention

The present invention generally relates to compounds that may be used to inhibit corrosion of metallic containers, such as those made of tin, aluminum, steel, or a combination thereof. More specifically, the present invention relates to such corrosion inhibiting compounds for use in cosmetics and other topically applied products.

2. Description of the Prior Art

Recent legislation and changing consumer preferences have lead to the development of cosmetics and other topically applied consumer products that have lower concentrations of volatile organic compounds (VOCs) compared to similar compositions of merely a decade ago. In general, newer compositions replace the less favored VOCs with water and/or other compounds, such as alcohol, that typically contain residual amounts of water. However, water creates a potential for metallic container corrosion that exponentially increases as the water content increases.

The mechanism of corrosion may be uniform, galvanic, intergranular, or concentrated. Such corrosion may manifest itself as crevice corrosion, pitting, selective leaching, or stress cracking. Corrosion usually occurs electrochemically, involving electron transfers away from metals that are being oxidized, and electron acceptance by substances that are reduced.

The main approaches to minimize corrosion from fluids in a metallic container are to (1) lower the concentration of oxygen, (2) lower the concentration of corrosive ions, such as chlorides and sulfates, (3) optimize the pH of the composition, (4) utilize corrosion inhibitors, and (5) use a combination of any or all of the previous four approaches.

Corrosion inhibitors may be used as a lining material on the inner surface of the metallic container or canister or may be incorporated into the composition. However, while corrosion inhibitors may reduce the rate of overall corrosion, the electrochemical conditions of the composition may shift such that stress corrosion cracking and/or pitting may occur.

Many corrosion inhibitors are unsuitable for use in cosmetics and other consumer product compositions because the corrosion inhibitors have an objectionable effect on the aesthetics and/or function of the composition in which it is incorporated. As an obvious example, chromates and dichromates are well known corrosion inhibitors, yet are very toxic to humans.

U.S. Pat. No. 3,992,318 to Gaupp, et al. describes a corrosion inhibitor that requires a combination of a water-soluble phosphonic acid or its salt, a water-soluble polyphosphate or alkali metal phosphate, and a water soluble polymer of acrylic acid and/or methacrylic acid. The Gaupp, et al. patent discloses that this corrosion inhibitor is suitable for aqueous systems, particularly cooling systems for heat-producing equipment.

U.S. Pat. No. 4,240,925 to Tait discloses a pitting corrosion inhibiting composition that requires a cathodic corrosion inhibitor that is a phosphoric acid ester, amide or amide-ester, and an anodic corrosion inhibitor that is an organic compound.

U.S. Pat. No. 4,052,160 to Cook, et al. discloses the use of phosphonocarboxylic acids as corrosion inhibitors and/or scale control agents.

U.S. Pat. No. 4,548,787 to Wilson et al. discloses compositions for inhibiting mineral scale and the corrosion of metals. The compositions have water-soluble salts of an acid that can be molybdic acid, tungstic acid, and selenic acids in combination with a water-soluble phosphate.

Czech Patent No. 262,475 describes single component varnishes that have, among other ingredients, Group II metal dihydrogen phosphates.

Czech Patent No. 244,376 describes corrosion inhibitors for closed water and water-alcohol cooling systems. The corrosion inhibitors have an inhibitor mixture that includes disodium hydrogen phosphate, sodium metasilicate, and 1,2,3-benzotriazole.

Chinese Application No. 1,103,655 describes an anticorrosive heat transfer composition for heat pipes. The composition has sodium hexametaphosphate, trisodium phosphate, and disodium hydrogen phosphate, among other ingredients.

There is a need for corrosion inhibitors for use in cosmetics and other consumer product compositions that are non-toxic, non-aromatic, invisible, and generally compatible with the extensive variety of compounds that are used in cosmetics and other consumer product compositions.

Applicants have surprising discovered that phosphate compositions may be used in cosmetics and other consumer product compositions to effectively inhibit corrosion, yet exhibit no undesirable aesthetic and/or functional attributes. Specifically, applicants have discovered that phosphates and/or polyphosphates are effective in cosmetics and other consumer product compositions when present in an amount about 0.05 percentage by weight (wt %) to about 1.5 wt % based on the total weight of the finished composition.

SUMMARY OF THE INVENTION

It is an object of the present invention to provide a cosmetic or other topical composition having a compound in an amount effective to inhibit corrosion of the composition's metallic container.

It is another object of the present invention to provide such a corrosion inhibiting compound that is non-toxic, substantially non-aromatic, and generally compatible with the finished, topically applied consumer composition.

Accordingly, there is provided a cosmetic or topical composition for use on the human body having a phosphate corrosion inhibitor in an amount effective to inhibit corrosion of metallic containers containing the composition. Preferably, such a cosmetic or topical composition has sodium hydrogen phosphates and/or sodium polyphosphates in an amount about 0.05 wt % to about 1.5 wt % based on the total weight of the finished composition.

DETAILED DESCRIPTION OF THE INVENTION

The present invention provides an inorganic corrosion inhibitor for use in cosmetics and other topically applied consumer product compositions, such as aerosol hair-care products.

Applicants have surprisingly discovered that phosphate compounds may be used as effective corrosion inhibitors in cosmetics and other compositions that are applied topically to the human body. In particular, applicants have surprisingly discovered that topical compositions incorporating phosphate compounds as the principle corrosion inhibiting agent, as opposed to other known corrosion inhibitors, were not impaired either aesthetically or functionally.

Accordingly, the composition of the present invention should not employ as the principle corrosion inhibiting agent compounds such as molybdate, selenate, tungstate, water-soluble silicate, siloxane-silicate copolymer, phosphonic acid, water-soluble polymer of acrylic and/or methacrylic acid, aluminum phosphate, ε-caprolactam, 1,2,3-benzatriazole, or an organic phosphate.

Phosphate compounds are compounds having at least one phosphate group ($PO_4^{3-}$). Similarly, phosphite compounds are compounds having at least one phosphite group ($PO_3^{3-}$). Polyphosphate compounds are compound having at least one polyphosphate group ($P_xO_{3x+1}^{(x+2)-}$), wherein x is an integer greater than 1, such as a pyrophosphate group ($P_2O_7^{4-}$). Accordingly, as used herein, unless stated otherwise, the term "phosphate" also includes phosphite and polyphosphate.

Preferred phosphate compounds according to the present invention are phosphate salts of alkali metals (Group IA), such as sodium phosphate, disodium phosphate, and potassium phosphate. In addition, phosphate compounds for use in a composition according to the present invention may also be phosphate salts of alkaline earth metals (Group IIA), such as magnesium phosphate and calcium phosphate.

A particularly useful phosphate salt of an alkali metal according to the present invention is disodium hydrogen phosphate. Disodium hydrogen phosphate is used in boiler water treatment, electrical plating, detergent manufacture, metal cleanser, and dye auxiliary. Food grade disodium hydrogen phosphate may be used in food treatment as an emulsifier, a nutrition intensifier, a buffer, and powder acidulant. Disodium hydrogen phosphate is also known as dibasic sodium phosphate and secondary sodium phosphate.

Another phosphate salt of an alkali metal that is particularly useful according to the present invention is sodium polyphosphate. Sodium polyphosphate is a mixture of sodium salts of polyphosphoric acid. Sodium polyphosphate is also known as sodium hexametaphosphate and sodium tripolyphosphate.

The phosphate compound may be present in the composition in an amount about 0.05 wt % to about 1.5 wt % based on the total weight of the composition. Preferably, the phosphate compound is present in an amount about 0.1 wt % to about 1.0 wt %, and more preferably about 0.1 wt % to about 0.5 wt %, based on the total weight of the composition. These ranges for the phosphate compound are effective for inhibiting corrosion when incorporated in a composition having water. In addition, these ranges for the phosphate compound are effective when the composition has an amount of water about 10 wt % to about 75 wt % based on the total weight of the composition.

The compositions of the present invention can be packaged in containers made from tin, aluminum, steel, or any combination thereof. The compositions of the present invention have been found to be particularly compatible with aluminum, which has heretofore presented a challenge to prior art, topically applied, consumer product compositions.

Tables 1 and 2 summarize the results of a screening process for appropriate corrosion inhibitors. A selected corrosion inhibitor was combined with a composition having a resin and no more than about 55 wt % VOCs, but without dimethyl ether propellant. The effect and potential for corrosion on unlined tin and unlined aluminum were visually assessed using an optical microscope. The effects and potential for corrosion on unlined tin and unlined aluminum were also assessed by a cyclic potentiodynamic polarization (CPP) test in accordance with ASTM G61, which is incorporated herein by reference. The CPP test is an accelerated electrochemical technique that provides an indication of the corrosion behavior of a metal exposed to a particular environment. In this case, a specimen from a metal container is exposed to a hair spray base formula in the corrosion cell. The potential between the specimen metal and a reference electrode is controlled and the ensuing current is measured. The cell is open to the atmosphere and the test is conducted at ambient temperature.

TABLE 1

Assessment of Corrosion of Unlined Tin by Hair Spray Concentrate having a Corrosion Inhibitor

| Corrosion Inhibitor | Visual Assessment | Optical Microscope Assessment | CPP Pitting Trend Assessment |
|---|---|---|---|
| No Inhibitor | small pit holes | uniform pitting | pitting |
| sodium selenate 0.19 wt % | no pitting | uniform pitting | pitting |
| sodium selenate 0.38 wt % | uniform pitting | uniform pitting | no pitting, but high risk of future pitting |
| sodium molybdate 0.19 wt % | uniform pitting | uniform pitting | no pitting, but high risk of future pitting |
| sodium molybdate 0.38 wt % | uniform pitting | uniform pitting | uniform pitting |
| ammonium molybdate 0.19 wt % | uniform pitting | uniform pitting | no pitting, but high risk of future pitting |
| ammonium molybdate 0.38 wt % | no pitting | no pitting | no pitting, but high risk of future pitting |
| MEA/MIPA borate 0.19 wt % | uniform pitting | uniform pitting | no pitting, but high risk of future pitting |
| MEA/MIPA borate 0.38 wt % | uniform pitting | uniform pitting | no pitting, but high risk of future pitting |
| sodium dihydrogen phosphate 0.19 wt % | no pitting | no pitting | no pitting |
| sodium dihydrogen phosphate 0.38 wt % | no pitting | no pitting | no pitting |

TABLE 2

Assessment of Corrosion of Unlined Aluminum by Hair Spray Concentrate having a Corrosion Inhibitor

| Corrosion Inhibitor | Visual Assessment | Optical Microscope Assessment | CPP Pitting Trend Assessment |
|---|---|---|---|
| No Inhibitor | uniform pitting | uniform pitting | pitting |
| sodium selenate 0.19 wt % | no pitting | uniform pitting | pitting |
| sodium selenate 0.38 wt % | uniform pitting | pitting | pitting |
| sodium molybdate 0.19 wt % | uniform pitting | pitting | pitting |
| sodium molybdate 0.38 wt % | uniform pitting | pitting | pitting |
| ammonium molybdate 0.19 wt % | no pitting | uniform pitting | no pitting, but high risk of future pitting |
| aluminum molybdate 0.38 wt % | no pitting | uniform pitting | pitting |
| MEA/MIPA borate 0.19 wt % | no pitting | uniform pitting | pitting |

TABLE 2-continued

Assessment of Corrosion of Unlined Aluminum by Hair Spray Concentrate having a Corrosion Inhibitor

| Corrosion Inhibitor | Visual Assessment | Optical Microscope Assessment | CPP Pitting Trend Assessment |
|---|---|---|---|
| MEA/MIPA borate 0.38 wt % | no pitting | no pitting | no pitting |
| sodium dihydrogen phosphate 0.19 wt % | no pitting | no pitting | no pitting |
| sodium dihydrogen phosphate 0.38 wt % | no pitting | no pitting | no pitting |

As stated above, certain ingredients in cosmetic and other topically applied consumer product composition will promote corrosion and/or counteract corrosion inhibitors within the composition. Resins are one such corrosion promoting ingredient. However, some resins are essential to the function of many cosmetic and topically applied consumer product compositions. Thus, careful selection of both the resin and corrosion inhibitor is necessary. Resins that may be used in the present invention include: acrylates copolymer, PVP-modified resin, vinyl acetate copolymers, vinyl alcohol copolymers, polyurethane film formers, isobutylene/ethylmaleimide/hydroxyethylmaleinide copolymers, acrylates/succinates/hydroxyesters acrylate copolymer, modified cornstarch, low molecular weight esters of PVM/MA copolymer, octylacrylamide/acrylates/butylaminoethyl methacrylate, polyurethanes and other resins that do not require neutralization, and any combination thereof. Resins that do not require neutralization are most preferred.

The following formulas are examples according to the present invention, which incorporate disodium hydrogen phosphate as a corrosion inhibitor. The compositions of the present invention preferably include an active ingredient selected from the group consisting of: a hair care active, a skin care active, a nail care active, a foot care active, a deodorant, an antiperspirant, a fragrance, an antimicrobial, an antifungal, an insect repellant, a sunscreen/UV absorber, and any combination thereof. These ingredients are provided in an amount effective to achieve the intended purpose of the composition. The composition may be an aerosol or a non-aerosol. When an aerosol, the composition may include up to 85% VOC, such as a propellant. Preferably, the composition has VOCs in an amount about 55% by weight or less based on the total weight of each composition.

FORMULA 1 - AEROSOL HAIR SPRAY

| INGREDIENT | FUNCTION | RANGE IN WT % |
|---|---|---|
| ALCOHOL SC 40B | Solvent | 35 to 60 |
| DEMINERALIZED WATER | Solvent | QS |
| AMPHOTERIC ACRYLIC RESIN | Hair Fixative | 1 to 5 |
| AMINOMETHYL PROPANOL - 95% | Neutralizing Agent for Resin | 0.4 to 0.85 |
| DIMETHICONE COPOLYOL | Conditioning Agent | 0.01 to .75 |
| FRAGRANCE | Fragrance | 0 to 1 |
| DISODIUM HYDROGEN PHOSPHATE | Corrosion Inhibitor | 0.15 to 1.5 |
| PROPELLANT (e.g., Dimethyl Ether) | Carrier | 30 to 75 |

FORMULA 2 - AEROSOL HAIR SPRAY

| INGREDIENT | FUNCTION | RANGE IN WT % |
|---|---|---|
| DEMINERALIZED WATER | Solvent | QS |
| ALCOHOL SD 40B | Solvent | 12 to 25 |
| ACRYLATES COPOLYMER | Hair Fixative | 5 to 11 |
| DIMETHICONE COPOLYOL | Conditioning Agent | 0.001 to .75 |
| DISODIUM HYDROGEN PHOSPHATE | Corrosion Inhibitor | 0.06 to 0.2 |
| AMINOMETHYL PROPANOL - 95% | Neutralizer for Resin | 0.3 to 1.2 |
| PROPELLANT (e.g., Dimethyl Ether) | Carrier | 30 to 40 |

FORMULA 3 - AEROSOL HAIR SPRAY

| INGREDIENT | FUNCTION | RANGE IN WT % |
|---|---|---|
| DEMINERALIZED WATER | Solvent | QS |
| ALCOHOL SD 40B | Solvent | 9 to 15 |
| DIMETHICONE COPOLYOL | Conditioners | 0.02 to 0.75 |
| FRAGRANCE | Fragrance | 0 to 0.6 |
| POLYURETHANE | Hair Fixative | 12 to 21 |
| AMINOMETHYL PROPANOL - 95% | Neutralizer for Resin | 0.3 to 1.2 |
| DISODIUM HYDROGEN PHOSPHATE | Corrosion Inhibitor | 0.06 to 0.2 |
| PROPELLENT (e.g., dimethyl ether) | Carrier | 30 to 40 |

FORMULA 4 - AEROSOL HAIR SPRAY

| INGREDIENT | FUNCTION | RANGE IN WT % |
|---|---|---|
| DEMINERALIZED WATER | Solvent | QS |
| ALCOHOL SD 40B ANHYDROUS | Solvent | 40 to 60 |
| ACRYLATES COPOLYMER | Hair Fixative, Resin | 9 to 14 |
| FRAGRANCE | Fragrance | 0 to 0.6 |
| DIMETHICONE | Conditioner | 0.02 to 0.75 |
| AMINOMETHYL PROPANOL - 95% | Neutralizer for Resin | 0.3 to 1.2 |
| DISODIUM HYDROGEN PHOSPHATE | Corrosion Inhibitor | 0.06 to 0.2 |
| PROPELLENT (e.g., dimethyl ether) | Carrier | 30 to 40 |

| FORMULA 5 - NON-AEROSOL HAIR SPRAY | | |
|---|---|---|
| INGREDIENT | FUNCTION | RANGE IN WT % |
| DEMINERALIZED WATER | Solvent, Diluent | QS |
| ALCOHOL SD 40B | Solvent, Diluent | 9 to 15 |
| AMINOMETHYL PROPANOL | Neutralizer for Resin | 0.25 to 1 |
| ACRYLATES/SUCCINATES/ HYDROXYESTERS | Hair Fixative, Resin | 9 to 15 |
| DIMETHICONE COPOLYOL | Conditioning Agent | 0.02 to 0.75 |
| FRAGRANCE | Fragrance | 0 to 0.04 |
| DISODIUM HYDROGEN PHOSPHATE | Corrosion Inhibitor | 0.05 to 0.2 |

| FORMULA 6 - AEROSOL STYLING MOUSSE | | |
|---|---|---|
| INGREDIENT | FUNCTION | RANGE IN WT % |
| DEMINERALIZED WATER | Solvent | QS |
| PROPYLENE GLYCOL | Foam Modifier | 0.03 to 2 |
| COCAMIDOPROPYL BETAINE | Foam Modifier | 0.15 to 2 |
| POE (20M) SORBITAN MONOLAURATE | Foam Modifier | 0.015 to 11 |
| DISODIUM EDTA | Preservative | 0.03 to 0.4 |
| METHYLPARABEN | Preservative | 0.03 to 0.6 |
| IMIDAZOLIDINYL UREA | Preservative | 0.03 to 0.3 |
| DIMETHICONE COPOLYOL | Conditioning Agents | 0.02 to 2 |
| PVP | Hair Fixative | 1 to 8 |
| POLYQUATERNIUM-11 | Hair Fixative | 0.1 to 2 |
| POTASSIUM HYDROXIDE | pH Adjuster | 0.0015 to 0.2 |
| FRAGRANCE | Fragrance | 0 to 1 |
| DISODIUM HYDROGEN PHOSPHATE | Corrosion Inhibitor | 0.15 to 1.5 |
| PROPELLANT (e.g., Dimethyl Ether) | Carrier | 30 to 75 |

| FORMULA 7 - AEROSOL DRY-OIL BODY-SPRAY | | |
|---|---|---|
| INGREDIENT | FUNCTION | RANGE IN WT % |
| ALCOHOL SD 40B | Diluent | 18 to 70 |
| WATER | Diluent | 1.5 to 8 |
| POP (14M) BUTYL ETHER | Surfactant | 0.5 to 7 |
| GLYCERIN | Moisturizer, Humectant | 0.15 to 7 |
| CYCLOMETHICONE-PENTAMER | Feel Modifier | 0.15 to 7 |
| ISOPROPYL PALMITATE | Moisturizer, Lubricant | 0.15 to 11 |
| FRAGRANCE | Fragrance | 0 to 2 |
| DISODIUM HYDROGEN PHOSPHATE | Corrosion Inhibitor | 0.15 to 1.5 |
| PROPELLANT (e.g., dimethyl ether) | Carrier | 30 to 75 |

| FORMULA 8 - AEROSOL DRY-OIL BODY-SPRAY | | |
|---|---|---|
| INGREDIENT | FUNCTION | RANGE IN WT % |
| ALCOHOL SD 40B | Diluent | 18 to 70 |
| WATER | Diluent | 1.5 to 8 |
| POP (14M) BUTYL ETHER | Surfactant | 0.5 to 7 |
| GLYCERIN | Moisturizer, Humectant | 0.15 to 7 |
| CYCLOMETHICONE-PENTAMER | Feel Modifier | 0.15 to 7 |
| ISOPROPYL PALMITATE | Moisturizer, Lubricant | 0.15 to 11 |
| FRAGRANCE | Fragrance | 0 to 2 |
| DISODIUM HYDROGEN PHOSPHATE | Corrosion Inhibitor | 0.15 to 1.5 |
| PROPELLANT (e.g., dimethyl ether) | Carrier | 30 to 75 |

| FORMULA 9 - AEROSOL FOOT-ODOR SPRAY | | |
|---|---|---|
| INGREDIENT | FUNCTION | RANGE IN WT % |
| ALCOHOL SD 40B ANHYDROUS | Diluent | 55 to 75 |
| MENTHOL | Cooling Ingredient, Fragrance | 0.025 to 1 |
| C12-15 ALCOHOLS BENZOATE | Emollient | |
| ACETYLATED LANOLIN ALCOHOL/OLEYL ALCOHOL | Emollients, Moisturizers | 0.3 to 15 |
| POLYETHYLENE GLYCOL 300/SODIUM BICARBONATE | Humectants/Moisturizer absorbers | 0.45 to 12 |
| ZINC PHENOLSULFONATE | Wound/Skin Healing Agent | 0.75 to 8 |
| TRICLOSAN | Antimicrobial | $\leq 1$ |
| BENTONITE | Viscosity Modifier | 0.25 to 4 |
| TALC - HIGH DENSITY | Moisturizer | 0.3 to 7.5 |
| FRAGRANCE | Fragrance | 0 to 3 |
| DISODIUM HYDROGEN PHOSPHATE | Corrosion Inhibitor | 0.15 to 1.5 |
| PROPELLANT (e.g., Dimethyl Ether) | Carrier | 30 to 75 |

FORMULA 10 - AEROSOL ANTIPERSPIRANT/DEODORANT

| INGREDIENT | FUNCTION | RANGE IN WT % |
|---|---|---|
| ISOPROPYL MYRISTATE | Emollient, Moisturizer | 9 to 45 |
| CYCLOMETHICONE - PENTAMER | Feel Modifier | 0.5 to 45 |
| ZINC STEARATE | Feel Modifier, Drying agent | 0.5 to 5 |
| ALUMINUM CHLOROHYDRATE | Antiperspirant | 1.5 to 30 |
| SILICON DIOXIDE - FUMED | Viscosity Modifier/ Drying agent | 0.15 to 4 |
| FRAGRANCE | Scent | 0 to 1 |
| DISODIUM HYDROGEN PHOSPHATE | Corrosion Inhibitor | 0.15 to 1.5 |
| PROPELLANT (e.g., Dimethyl Ether) | Carrier | 30 to 75 |

FORMULA 11 - AEROSOL INSECT REPELLENT

| INGREDIENT | FUNCTION | WT % |
|---|---|---|
| ETHYL BUTYLACETYL AMINOPROPRIONATE | Insect repellent | 25 |
| N,N DIETHYLTOLUAMIDE | Insect repellent | 25 |
| DISODIUM HYDROGEN PHOSPHATE | Corrosion Inhibitor | 1 |
| PROPELLANT (e.g., dimethyl ether) | Carrier | 35 |
| WATER | Diluent | 14 |

FORMULA 12 - AEROSOL INSECT REPELLENT

| INGREDIENT | FUNCTION | WT % |
|---|---|---|
| P-METHANE DIOL | Insect Repellent | 20 |
| OIL OF CITRONELLA | Insect Repellent | 10 |
| DISODIUM HYDROGEN PHOSPHATE | Corrosion Inhibitor | 0.75 |
| PROPELLANT | Carrier | 30 |
| WATER | Diluent | 39.25 |

The present invention having been thus described with particular reference to a preferred form thereof, it will be obvious that various changes and modifications may be made therein without departing from the spirit and scope of the present invention as defined in the appended claims.

Therefore we claim:

1. A topical composition comprising:
    an active ingredient selected from the group consisting of a hair care active, a skin care active, a nail care active, a foot care active, a deodorant, an antiperspirant, a fragrance, an antimicrobial, an antifungal, an insect repellent, a sunscreen/UV absorber, and any combinations thereof;
    water;
    a phosphate compound selected from the group consisting of disodium hydrogen phosphate, an alkali metal salt of a polyphosphate, and any combination thereof;
    a cosmetically acceptable vehicle; and
    volatile organic compounds,
    wherein said phosphate compound is present in an amount effective to inhibit corrosion of a metallic container holding the composition.

2. The composition of claim 1, wherein said volatile organic compounds are present in an amount not greater than about 85 wt % based on the total weight of the composition.

3. The composition of claim 1, wherein said volatile organic compounds are present in an amount not greater than about 55 wt % based on the total weight of the composition.

4. The composition of claim 1, further comprising a propellant.

5. A method of inhibiting corrosion of a metallic container holding a composition comprising water and an active ingredient selected from the group consisting of a hair care active, a skin care active, a nail care active, a foot care active, a deodorant, an antiperspirant, a fragrance, an antimicrobial, an antifungal, an insect repellent, a sunscreen/UV absorber, and any combinations thereof, said method comprising the step of:
    adding a phosphate compound to the composition in an amount effective to inhibit corrosion of the metallic container, wherein the phosphate compound is an alkali metal or alkaline earth metal salt of a phosphate or polyphosphate.

6. The method of claim 5, wherein said phosphate compound is an alkali metal salt of a phosphate.

7. The method of claim 6, wherein said alkali metal salt of a phosphate is disodium hydrogen phosphate.

8. The method of claim 5, wherein said phosphate compound is an alkaline earth metal salt of a phosphate.

9. The method of claim 5, wherein said phosphate compound is present in an amount about 0.05 wt % to about 1.5 wt % based on the total weight of the composition.

10. The method of claim 5, wherein said phosphate compound is present in an amount about 0.1 wt % to about 1.0 wt % based on the total weight of the composition.

11. A system comprising:
    a metallic container being made from a material selected from the group consisting of tin, aluminum, steel, and any combinations thereof; and
    a composition having:
    an active ingredient selected from the group consisting of a hair care active, a skin care active, a nail care active, a foot care active, a deodorant, an antiperspirant, a fragrance, an antimicrobial, an antifungal, an insect repellent, a sunscreen/UV absorber, and any combinations thereof;
    water;
    a cosmetically acceptable vehicle; and
    a principle corrosion inhibiting agent in an amount effective to inhibit corrosion of the metallic container, wherein the principle corrosion inhibiting agent is a phosphate compound selected from the group consisting of disodium hydrogen phosphate, an alkali metal salt of a polyphosphate, and a combination thereof.

12. The system of claim 11, wherein the container is an aerosol spray container, and wherein the composition further comprises a propellant.

13. The system of claim 11, wherein the phosphate compound is the alkali metal or alkaline earth metal salt of a phosphate or a polyphosphate.

14. The system of claim 11, wherein said phosphate compound is an alkali metal salt of a phosphate.

15. The system of claim 14, wherein said alkali metal salt of a phosphate is disodium hydrogen phosphate.

16. The system of claim 11, wherein said phosphate compound is an alkaline earth metal salt of a phosphate.

17. The system of claim 11, wherein said phosphate compound is present in an amount about 0.05 wt % to about 1.5 wt % based on the total weight of the composition.

18. The system of claim 11, wherein said phosphate compound is present in an amount about 0.1 wt % to about 1.0 wt % based on the total weight of the composition.

19. The system of claim 11, wherein the composition further comprises volatile organic compounds in an amount not greater than about 85 wt % based on the total weight of the composition.

20. The system of claim 11, wherein the composition further comprises volatile organic compounds in an amount not greater than about 55 wt % based on the total weight of the composition.

21. The system of claim 11, wherein the container is made of aluminum.

22. The system of claim 11, wherein the container is made from material having tin.

23. The system of claim 11, wherein the container is made from a material having aluminum.

24. The system of claim 11, wherein the container is made from a material having steel.

25. The system of claim 11, wherein said phosphate compound is present in an amount about 0.1 wt % to about 0.5 wt % based on the total weight of the composition.

26. A topical composition comprising:
an active ingredient selected from the group consisting of a hair care active, a skin care active, a nail care active, a foot care active, a deodorant, an antiperspirant, a fragrance, an antimicrobial, an antifungal, an insect repellent, a sunscreen/UV absorber, and any combinations thereof;
water;
a phosphate compound selected from the group consisting of disodium hydrogen phosphate, an alkali metal salt of a polyphosphate, and any combination thereof;
a cosmetically acceptable vehicle; and
a propellant,
wherein said phosphate compound is present in an amount effective to inhibit corrosion of a metallic container holding the composition.

27. The composition of claim 26, further comprising volatile organic compounds in an amount not greater than about 85 wt % based on the total weight of the composition.

28. The ccmposition of claim 26, further comprising volatile organic compounds in an amount not greater than about 55 wt % based on the total weight of the composition.

29. A topical composition conprising:
an active ingredient selected from the group consisting of a hair care active, a skin care active, a nail care active, a foot care active, a deodorant, an antiperspirant, a fragrance, an antimicrobial, an antifungal, an insect repellent, a sunscreen/UV absorber, and any combinations thereof;
water;
a phosphate compound selected from the group consisting of disodium hydrogen phosphate, an alkali metal salt of a polyphosphate, and any combination thereof;
a cosmetically acceptabie vehicle;
a volatile organic compound; and
a propellant,
wherein said phosphate compound is present in an amount effective to inhibit corrosion of a metallic container holding the composition, said metallic container being made of a metal selected from the group consisting of tin, steel, aluminum and any combinations thereof.

* * * * *